(12) United States Patent
Fredenberg et al.

(10) Patent No.: US 9,486,175 B2
(45) Date of Patent: Nov. 8, 2016

(54) PHASE CONTRAST IMAGING APPARATUS

(75) Inventors: Erik Fredenberg, Stockholm (SE);
Magnus Aslund, Enebyberg (SE)

(73) Assignee: KONINKLIJKE PHILIPS N.V.,
Eindhoven (NL)

( * ) Notice: Subject to any disclaimer, the term of this patent is extended or adjusted under 35 U.S.C. 154(b) by 156 days.

(21) Appl. No.: 14/126,214

(22) PCT Filed: Jun. 27, 2012

(86) PCT No.: PCT/EP2012/062489
§ 371 (c)(1),
(2), (4) Date: Jan. 27, 2014

(87) PCT Pub. No.: WO2013/004574
PCT Pub. Date: Jan. 10, 2013

(65) Prior Publication Data
US 2014/0146945 A1 May 29, 2014

Related U.S. Application Data

(60) Provisional application No. 61/504,260, filed on Jul. 4, 2011.

(30) Foreign Application Priority Data

Jul. 4, 2011 (SE) .................................... 1150322-7

(51) Int. Cl.
*A61B 6/00* (2006.01)
*A61B 6/06* (2006.01)
*A61B 6/04* (2006.01)

(52) U.S. Cl.
CPC .............. *A61B 6/484* (2013.01); *A61B 6/4233* (2013.01); *A61B 6/4241* (2013.01);
(Continued)

(58) Field of Classification Search
CPC .... A61B 6/484; A61B 6/482; A61B 6/4291; A61B 6/4241; A61B 6/4233; A61B 6/4441; A61B 6/06; A61B 6/0414; A61B 6/5205; A61B 6/582; A61B 6/502; A61B 6/4035; G21K 2207/005
See application file for complete search history.

(56) References Cited

U.S. PATENT DOCUMENTS 5,335,255 A * 8/1994 Seppi .................... A61B 6/032
378/134
5,812,629 A 9/1998 Clauser
(Continued)

FOREIGN PATENT DOCUMENTS

JP 2008206560 A 9/2008
WO 2008006470 A1 1/2008

OTHER PUBLICATIONS

Kottler et al: "Grating Interferometer Based Scanning Setup for Hard X-Ray Phase Contrast Imaging"; Review of Scietific Instruments, AIP, vol. 78, No. 4, April 2007, pp. 43710-43710.

*Primary Examiner* — Brooke Purinton

(57) ABSTRACT

An x-ray imaging system includes an x-ray source, an x-ray detector including a plurality of detector strips arranged in a first direction of the x-ray detector. Each detector strip includes a plurality of detector pixels arranged in a second direction of the x-ray detector. A phase grating and a plurality of analyzer gratings including grating slits are disposed between the x-ray source and detectors. The x-ray source and the x-ray detector are adapted to perform a scanning movement in relation to an object in the first direction, in order to scan the object. Each of the plurality of analyzer gratings (162) is arranged in association with a respective detector strip with the grating slits arranged in the second direction. The grating slits of the analyzer gratings of the detector strips are offset relative to each other in the second direction.

12 Claims, 6 Drawing Sheets

(52) U.S. Cl.
CPC ............ *A61B 6/4291* (2013.01); *A61B 6/482* (2013.01); *A61B 6/0414* (2013.01); *A61B 6/06* (2013.01); *A61B 6/4441* (2013.01); *A61B 6/502* (2013.01); *A61B 6/5205* (2013.01); *A61B 6/582* (2013.01)

(56) References Cited

U.S. PATENT DOCUMENTS

| | | |
|---|---|---|
| 7,496,176 B2 | 2/2009 | Aslund |
| 2007/0183560 A1 | 8/2007 | Popescu et al. |
| 2009/0128830 A1 | 5/2009 | Kottler et al. |
| 2010/0080436 A1 | 4/2010 | Ohara |
| 2010/0091936 A1 | 4/2010 | David et al. |
| 2010/0111395 A1* | 5/2010 | Tamakoshi ............ A61B 6/469 382/132 |
| 2010/0220832 A1 | 9/2010 | Ning et al. |
| 2012/0288056 A1* | 11/2012 | Murakoshi ........... A61B 6/4233 378/37 |
| 2013/0010926 A1* | 1/2013 | Tada ........................ A61B 6/06 378/62 |
| 2014/0112440 A1* | 4/2014 | David .................. A61B 6/4035 378/62 |

* cited by examiner

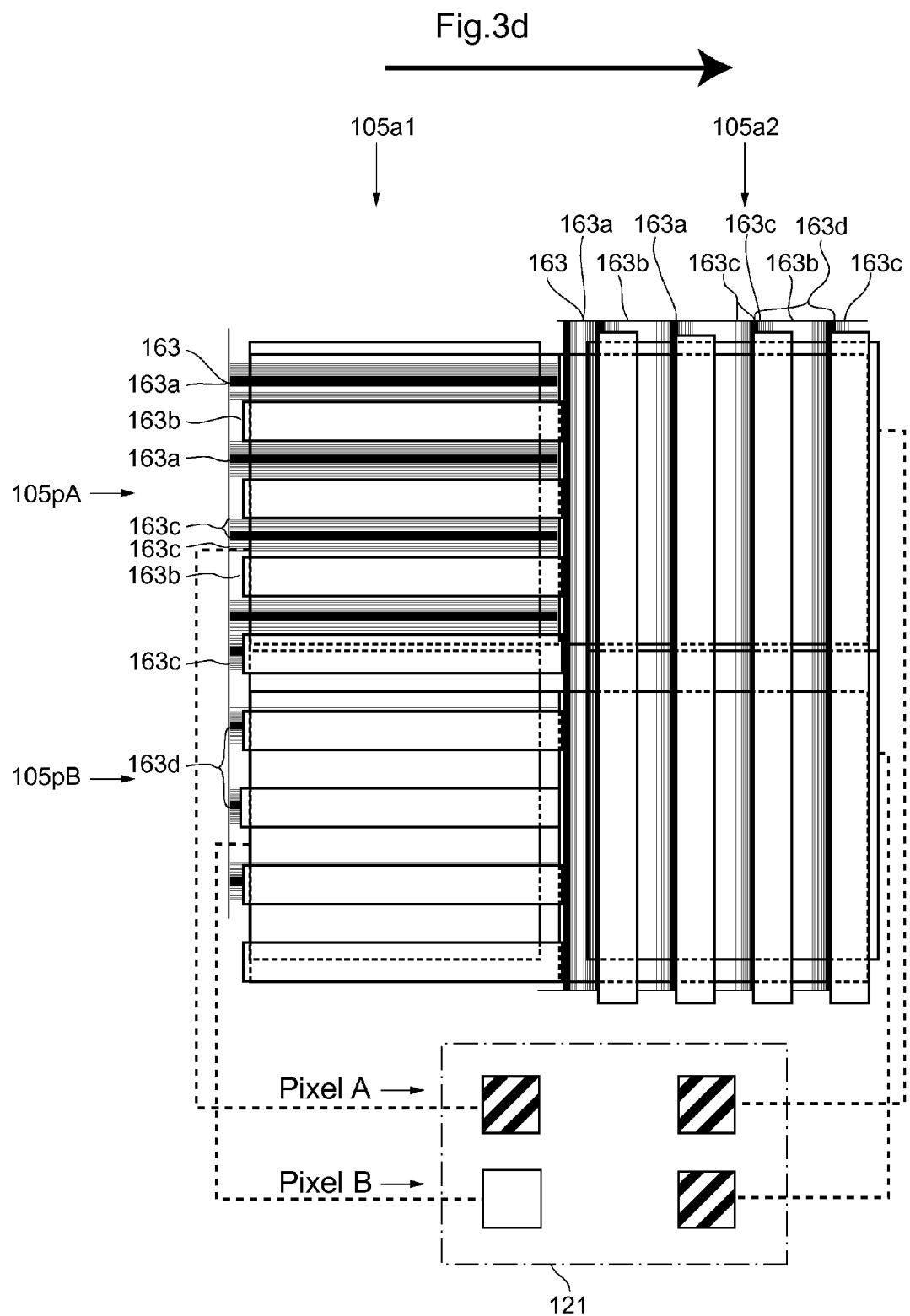

PHASE CONTRAST IMAGING APPARATUS

CROSS-REFERENCE TO PRIOR APPLICATIONS

This application is the U.S. National Phase application under 35 U.S.C. §371 of International Application No. PCT/EP2012/062489, filed on Jun. 27, 2012, which claims the benefit of U.S. Provisional Patent Application No. 61/504,260, filed on Jul. 4, 2011 and SE Provisional Patent Application No. 1150622-7, filed on Jul. 4, 2011. These applications are hereby incorporated by reference herein in their entirety.

TECHNICAL FIELD

The present invention relates generally to an improved x-ray imaging apparatus in the field of mammography, tomosynthesis, radiography, wherein phase contrast imaging capabilities have been implemented.

BACKGROUND ART

In prior art it has been proposed to use phase contrast in x-ray imaging to increase signal-to-noise ratio (SNR) in e.g. mammographic applications. Medical x-ray imaging is often limited by small contrast differences and high noise caused by tight dose restraints. This is particularly true for mammography where low contrast tumors constitute a major detection target, and a large number of tumors are missed or misdiagnosed due to difficulties in detection. The use of phase contrast imaging in medical applications have shown promising in order to increase SNR, since the phase shift in soft tissue is in many cases substantially larger than the absorption.

International patent application WO 2008/006470 A1 describes the use of interferometers for x-rays wherein x-ray images can be acquired from a scanned object. The set up herein comprises means for evaluating intensities on a pixel 105p basis in order to identify characteristic of the object 108 by characterizing each pixel 105p as being for instance phase contrast or absorption contrast dominated. In one application concerning the investigation of luggage on a moving conveyor belt, a set-up comprising an array of line detector 105s and a number of sub-gratings are arranged between the object 108 and the line detector 105s wherein each of the sub-gratings are shifted in their position perpendicular to the grating lines. In this manner, luggage to be investigated is moved along a direction perpendicular to the grating lines during a scan, wherein one scan movement is required to acquire phase contrast and absorption contrast data.

There are a number of disadvantages with the art presented above. First of all, the solution requires the manufacturing of physically long sub-gratings $G1_n$ and $G2_n$, which is consumes resources in terms of cost and time.

Another drawback is that the proposed set up if directly implemented in a mammography application is likely to induce errors in the phase detection due to the direction of the scan vs the direction of phase contrast detection. When a stationary object 108 such as a breast is analyzed, the set up needs to be moved in a scan direction in relation to the object 108 to create an x-ray image of the object, not the other way around as in WO 2008/006470 A1. In WO 2008/006470 A1, the scan direction is set to be perpendicular to the grating lines of the sub-gratings, and hence perpendicular to the interference fringes 163 to be detected.

It is well known that any system, including scanning systems, generally introduce more disturbances in the scan direction since this is the direction of change. Another source of disturbance is the gravity itself on a moving scan arm 103, since a gravity component of the scan arm 103 will induce a torque on a detector 105/analyzer grating 162 relative to the beam 122 splitter. Hence, a small shift between the analyzer grating 162 and the beam 122 splitter due to gravitation will further induce errors in the phase detection. In conclusion, in order to reduce these disturbances a set up as in the prior art needs have very high requirements on scan precision, which will make the manufacturing of such products more costly as well as time-consuming.

Yet another drawback of the prior art is that the full potential of using phase contrast, especially sought for in mammographic applications, is not utilized. One of the main advantages of using phase contrast imaging is the reduced noise at high spatial frequencies, i.e. an improved ability to detect small features. In a scanning system, spatial resolution is generally lower in the scan direction since continuous read out is most often implemented.

SUMMARY OF INVENTION

An object of the present invention is to alleviate some of the disadvantages of the prior art and to provide an improved device for x-ray imaging. According to one embodiment, the x-ray imaging system comprises an x-ray source, an x-ray detector comprising a plurality of detector strips arranged in a first direction of the x-ray detector, each detector strip further comprising a plurality of detector pixels arranged in a second direction of the x-ray detector; a phase grating; a plurality of analyzer gratings comprising grating slits; a phase grating, and a plurality of analyzer gratings comprising grating slits, wherein the x-ray source and the x-ray detector are adapted to perform a scanning movement in relation to an object in the first direction, in order to scan the object, wherein the analyzer gratings are arranged between the x-ray source and the x-ray detector, wherein each of the plurality of analyzer gratings (162) is arranged in association with a respective detector strip with the grating slits arranged in the second direction and wherein the grating slits of the analyzer gratings of the detector strips are displaced relative to each other in the second direction.

According to another embodiment, the x-ray imaging system (101) comprises an x-ray source (104), an x-ray detector (105) (1 comprising a plurality of detector strips (105)a) arranged in a first direction of the x-ray detector (105), each detector strip (105)a further comprising a plurality of detector (105) pixels (105p) arranged in a second direction of the x-ray detector (105); a phase grating (161); and a plurality of analyzer gratings (162) comprising grating slits; wherein the (1) x-ray source (104) and the x-ray detector (105) are adapted to perform a scanning movement in relation to an object (108) in the first direction, in order to scan the object; wherein the analyzer gratings (162) are arranged between the x-ray source (104) and the x-ray detector (105), wherein a plurality of analyzer gratings (162) is arranged in association with a respective detector strip (105a) with the grating slits arranged in the second direction and wherein the grating slits of the analyzer gratings (162) of the detector strips (105a) are displaced relative to each other in the second direction.

According to another embodiment, the displacement of grating slits of the analyzer gratings (162) along a plurality of detector strips (105a) samples an entire fringe period (163d) of interference fringes (163) generated by a phase grating and displaced by a phase gradient in the object (108) when the object (108) is scanned.

According to another embodiment, the grating slits of analyzer gratings of two consecutive detector strips with analyzer gratings in a first direction are displaced relative to each other in the second direction in a systematic manner, wherein the systematic manner comprises a defined displacement distance.

According to another embodiment, the displacement distance (d) is a fraction of the fringe period $p_f$, such that $$\frac{p_f}{N} < d < p_f,$$

where N is the number of detector strips such that the entire fringe period 163d is covered.

According to another embodiment, the displacement distance (d) is between, $$\frac{p_f}{3} < d < p_f,$$

preferably $$\frac{p_f}{3}.$$

According to another embodiment, the grating slits of analyzer gratings of two consecutive detector strips are displaced relative to each other in the second direction in an arbitrary manner, wherein the arbitrary manner comprises a random displacement.

According to another embodiment, the grating slits of the randomly displaced analyzer gratings (162), when summarized, are uniformly distributed over an entire fringe period.

According to another embodiment, two consecutive detector strips with analyzer gratings in a first direction are two adjacent detector strips.

According to another embodiment, two consecutive detector strips (105a) with analyzer gratings (162) in a first direction are randomly or arbitrarily displaced among the detector strips (105a) in a first direction.

According to another embodiment, the system is adapted to be calibrated such that the exact position of the analyzer gratings is established.

According to another embodiment, analyzer gratings are arranged on all detector strips.

According to another embodiment, system further comprises a pre-collimator and a post-collimator, wherein the pre-collimator is arranged between the analyzer grating and the phase grating and the post-collimator is arranged between the analyzer grating and the x-ray detector.

According to another embodiment, the system further comprises a source grating arranged between the x-ray source and the phase grating.

According to another embodiment, the detector (105) is adapted to count photons impinging on the detector strips (105a) and generate a signal corresponding to the energy of impinging photons, and wherein a control unit (121) is adapted to receive said signals and assign a weight to the phase-contrast image effect in relation to the efficiency at each energy and/or wherein the control unit 121 is adapted to assign a weight to the phase-contrast image effect in relation to the efficiency at each energy.

According to another embodiment, the control unit (121) is adapted to assign a higher weight of photons within a first energy interval to the phase-contrast image effect wherein phase contrast is more optimal, and/or wherein the control unit is adapted to assign a higher weight of photons within a second energy interval to the absorption contrast effect, wherein absorption contrast is more optimal.

According to another embodiment, the first and second energy intervals are defined by a first, lower threshold value of the photon energy, and a second, higher threshold value of the photon energy, wherein each detector pixel of each detector strip is connected to a comparator and counter comprising at least two threshold values for comparing the signal with said threshold values and counting said photons within the first and second energy intervals.

According to another embodiment, that the detector is adapted to count each photon impinging on the detector strips and generate a signal corresponding to the energy of each impinging photon, and wherein photons within an energy interval comprising a lower energy threshold, a higher energy threshold, wherein the interval comprises an optimal energy for phase contrast are readout to enhance the phase contrast image effect According to another embodiment, that the energy distribution depends on the set voltage of the x-ray source or on the breast thickness, wherein the control unit is adapted to receive signals comprising information regarding the set voltage and/or receive signals comprising information regarding the breast thickness, for instance from an automated exposure control which optimizes the voltage based on the thickness of the object, and adapts the lower energy threshold and the higher energy threshold based on this information.

According to another embodiment, first energy interval contains higher photon energies than the second energy interval.

According to another embodiment, at least one analyzer grating is arranged in a first crosswise direction over the entire detector.

According to another embodiment, the system further comprises at least one movable compression paddle, wherein the compression paddle is adapted to move an object, such as a breast, further away from the analyzer grating to increase the phase contrast image effect.

According to another embodiment, the at least one compression paddle is adapted to move the object within a range between the analyzer grating and the pre-collimator or the phase grating.

According to another embodiment, the system further comprises a control unit adapted to move the compression paddle into a position wherein the ratio of the phase contrast and absorption contrast is optimized.

According to another embodiment, the at least one compression paddle is adapted to be arranged below an object.

According to another embodiment, a scan arm is provided, wherein the x-ray source is arranged in a first position of the scan arm and the x-ray detector is arranged in a second position of the scan arm.

According to another embodiment, the phase grating is arranged on the scan arm in order to follow the scan arm during the scanning movement in relation to an object in the first direction.

According to another embodiment, the phase grating is arranged to be stationary wherein the scan arm during the scanning movement is moved in relation to an object and the phase grating in the first direction.

According to another embodiment, the analyzer grating is arranged on each of a plurality of detector strips.

According to another embodiment, the analyzer grating is connected to each of a plurality of detector strips by a snap-fit like connection.

According to another embodiment, the analyzer gratings (162) are arranged directed towards the x-ray source (104), wherein the tilting direction of the analyzer gratings (162) are essentially equal to the tilting angle(s) of the plurality of detector strips (105a) in relation to the x-ray source (104)

According to another embodiment, each analyzer grating 162 comprises several smaller units, adapted to be connected to each other during the manufacturing of the analyzer gratings 162.

BRIEF DESCRIPTION OF DRAWINGS

The invention is now described, by way of example, with reference to the accompanying drawings, in which:

FIG. 3d shows a portion of the detector and a systematic displacement of the analyzer grating arranged in a perpendicular direction in a cross-wise manner

DESCRIPTION OF EMBODIMENTS

In the following, a detailed description of the invention will be given.

Figure 1:
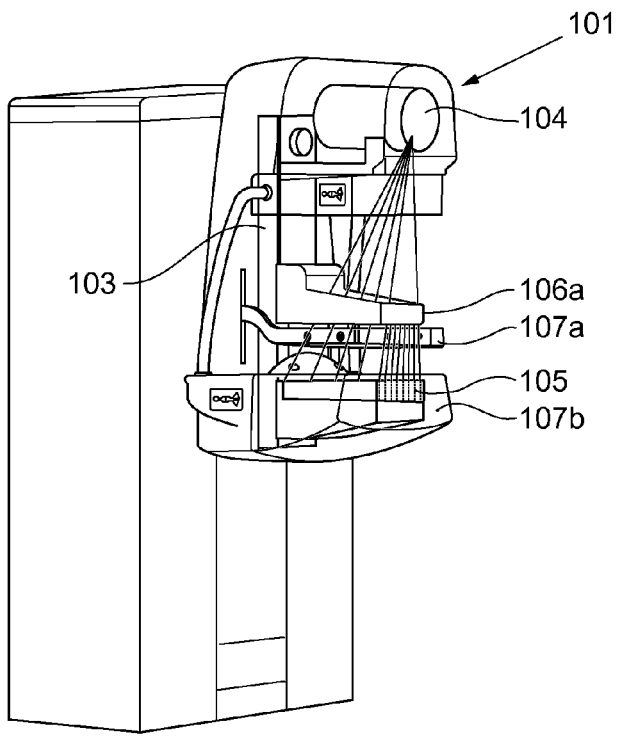
FIG. 1 shows a perspective view of an x-ray imaging system

FIG. 1 illustrates an x-ray imaging system 101 according to one embodiment, based on a photon-counting detector 105 that scans the image field in one direction. The system according to this embodiment is based on the existing scanning systems for x-ray imaging developed by the applicant, whereby the system have the same external features as are for instance known from document U.S. Pat. No. 7,496, 176. The system thus comprises an x-ray source 104 arranged in a housing, patient support and pre-collimator 106a housing and compression paddle 107a, 107b. A collimator is arranged in a collimator support, and the patient support comprises a detector 105 comprising a plurality of detector strips 105a. The x-ray source 104 and the detector 105 are arranged essentially in respective ends of a scan arm 103, hence arranged to be displaced radially with the x-ray source 104 in the centre. An image is acquired by scanning the detector 105 across an image field and applying absorption contrast principles. Whenever the detector 105 has scanned a predefined distance, the number of photon counts collected is read-out and the counter is reset. However any other type of x-ray system may implement the phase contrast imaging capability described herein, preferably systems with a scan movement to cover and generate an image of an object, by irradiating the object with x-ray beams.

Figure 2A:
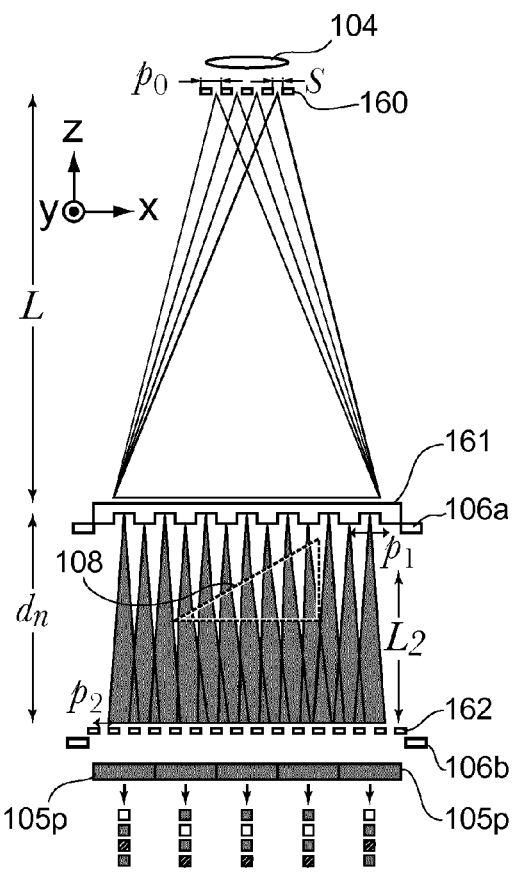
FIG. 2a shows a schematic view of the x-ray imaging system set up in a x-z-plane, corresponding to the phase contrast plane

FIG. 2a, disclosing one embodiment of the invention, shows a schematic view of a cross-section of the x-ray imaging system 101 enabling phase contrast imaging, set up in a x-z plane as defined by the coordinate system seen in the figure. The system according to this embodiment comprises a Talbot interferometer set up, and is thus based on so-called Talbot interferometry, also known as grating interferometry, grating-based phase contrast imaging, or differential phase contrast imaging, wherein phase shift is inferred by intensity differences, generated by placing a number of gratings in the beam 122 path. The scan direction along a radial path, with the x-ray source 104 in the center as seen in FIG. 1, is defined to be in the y-z plane, denoted by the arrow in FIG. 2b. In FIG. 2a the x-ray source 104 is arranged at the uppermost position of the system radiating the detector 105 arranged at the lowermost position in the figure. The x-ray source 104 emits an x-ray radiation beam 122. In one embodiment, a source grating 160 is arranged slightly displaced from the x-ray source 104 in the direction of the x-ray radiation field towards the detector 105. The source grating 160 lines extends in a y-direction. The purpose of the source grating 160 is to generate an array of small x-ray sources 104, which improves photon economy substantially compared to a single small x-ray source 104 without reducing coherence. Further down in the direction of the x-ray radiation field, a phase grating 161, sometimes denoted beam 122 splitter, is arranged with the purpose to introduce an effect known as Talbot self images, which are interference fringes 163 that appear at periodic distances from the grating and parallel with the grating strips, also known as grating lines. A pre-collimator 106a may be arranged essentially adjacent the phase grating 161, as seen in this embodiment to further enhance dose efficiency by illuminating only the parts of the object that can be seen with the detector. To facilitate the understanding of the workings of the phase contrast effect, an exemplary triangularly shaped object 108 is arranged between the phase grating 161 and the detector 105 according to this embodiment, however said object 108 but may also be arranged between the x-ray source 104 and the phase grating 161 and achieve similar effects. The object 108 corresponds to e.g. a breast in a mammography application. Slightly above the detector 105 as seen in a direction towards the phase grating 161, an analyzer grating 162 is arranged. The analyzer grating lines 162a extends in first direction corresponding to the scan direction y, whereas a plurality of grating slits, i.e. openings 162b, of the analyzer grating 162 extends in a second direction x, perpendicular to the scan direction, whereas the analyzer grating 162 extends a longer distance in the first direction than in the second direction. The pitch 162d of the analyzer grating 162 is referred to as the distance between the center of two adjacent closures 162c of the grating as can be seen in FIG. 2a, or in other words, as the total length of the width of one opening and one closure 162c in the grating. Between the analyzer grating 162 and the detector 105 a second post-collimator 106b may be arranged to further reduce photon scattering and thereby improve dose efficiency. Thus, as seen in the figure, the phase grating 161 is illuminated by the x-ray source 104 which is covered by a source grating 160 and induces interference fringes 163. The fringes 163 are displaced by the phase gradient, i.e. the derivative of the phase shift, in the object, and the fringe period 163d remains constant. The fine-pitch 162d analyzer grating 162 arranged in association with the detector 105 can be used to derive the fringe displacement and hence the phase shift.

For a spherical beam 122 induced by a point source, the so-called Talbot distances are:

$$d_n = \frac{D_n L}{L - D_n}, \text{ where } D_n = \frac{n p_1^2}{2\eta^2 \lambda}, n = 1, 3, 5, \ldots$$

Here, L is the source-to-grating distance, n is the Talbot order, $p_1$ is the pitch 162d of the phase grating 161, $\lambda$ is the x-ray wavelength, and $\eta$ is the parameter that depends on the phase grating 161 type.

Assuming a $\pi$ phase-shifting phase grating 161 according to one embodiment, which implies $\eta=2$. For a $\pi/2$-shifting phase grating 161, $\eta=1$.

The period of the interference fringes 163 is $$p_f = \frac{P_f L}{L - D_n}, \text{ where } P_f = \frac{p_1}{\eta}$$

Again, $P_f = p_f(L \to \infty)$ is the fringe period 163d for a plane incident wave. If the source is covered with a source grating 160 with openings 162b that are s wide and with a pitch 162d of $$p_0 = p_f \frac{L}{D_n}$$

The Talbot images generated from the different source slits coincide and generate a higher flux, which is of relevance to keep down the exposure time in phase-contrast imaging.

When a phase shifting object 108 is introduced in the beam 122, it is refracted an angle $\alpha = \Phi' \lambda / 2\pi$, where $\Phi'$ is the differential phase shift of the object. For small $\alpha$, the refraction causes a fringe displacement $$\Delta p_f \approx \Lambda d_n \times \alpha = \Lambda d_n \frac{\lambda}{2\pi} \Phi'$$

at a distance $\Lambda d_n$ from the object, where $\Lambda$ ranges from 0 for an object 108 placed in contact with the detector 105 to 1 for an object 108 at or upstream of the phase grating 161. The fringes 163 are periodic as a function of x, i.e. in the x direction in the set up according to the embodiment. Thus, a phase gradient in the object 108 causes a phase shift of the fringes 163, which can be measured to obtain $\Phi'$ by the intensity variations sensed behind the analyzer gratings 162. The phase shift $\Phi$ may be obtained by integration of $\Phi'$. The placing of the analyzer gratings 162 before the detector 105 is not theoretically necessary in order for a detector 105 to sense the fringe displacement; however it reduces the resolution requirement of the detector 105. Detectors 105 with enough resolution to detect $\Delta p_f$ may in fact be difficult and expensive to manufacture. One method used in the past comprising the analyzer grating 162 is the step-wise movement of the analyzer grating 162 in the x-direction until the entire fringe period 163d is covered by the openings 162b of the analyzer grating 162, preferably in at least M=3 measurements or steps. Such methods are normally referred to as phase stepping methods.

Figure 2B:
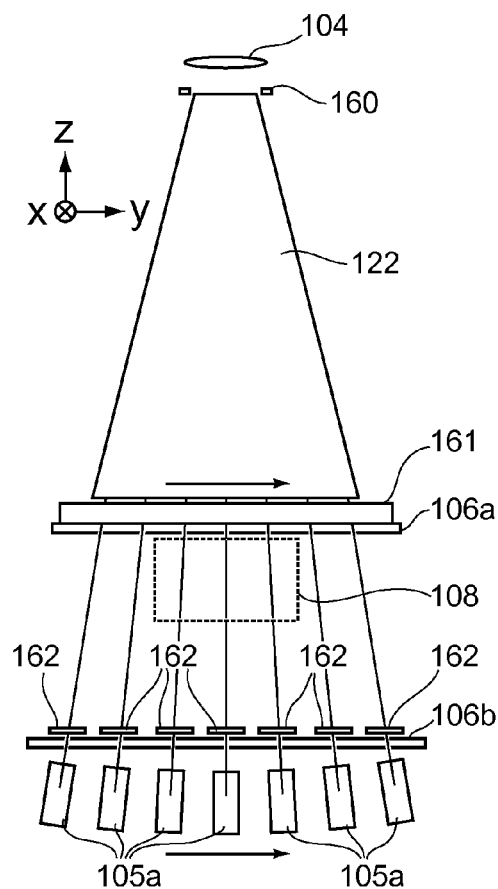
FIG. 2b shows a schematic view of the x-ray imaging system set up as seen in FIG. 2a in a y-z plane, corresponding to the absorption contrast plane

FIG. 2b shows a cross-section of the schematic view of the x-ray imaging system 101 set up as seen in FIG. 2a in a y-z plane. From this direction, it is made clear that the set up comprises a multi-slit geometry, according to well-known principles developed by the applicant, wherein the detector 105 comprises a plurality of Si strip detector 105s aligned with each of the plurality of slits of the pre-collimator 106a and post-collimator 106b. According to one embodiment, 21 strip detectors 105 are preferably used in a detector 105. Above and in association to each of a plurality of the detector strips 105a, analyzer gratings 162 have been arranged. As stated earlier, a scanning movement takes place in the y-z plane, essentially in the y-direction, as is also shown by the arrows in the figure. This direction is thus adapted to measure absorption contrast of an object, which will be further described below. According to one embodiment, the analyzer gratings are directed towards the x-ray source to minimize losses caused by the high aspect ratio of the analyzer gratings, i.e. in order to increase the dose efficiency and reduce scatter, the openings of the analyzer gratings are made more aligned with the direction of the x-ray beams. According to one embodiment, such direction may require tilting of the analyzer gratings such that they essentially have their opening perpendicular to the incident x-ray beams, similar to the direction of the surface of each detector strip 105a.

According to one embodiment, each analyzer grating 162 comprises several smaller units, adapted to be connected to each other during the manufacturing of the analyzer gratings 162.

Figure 3A:
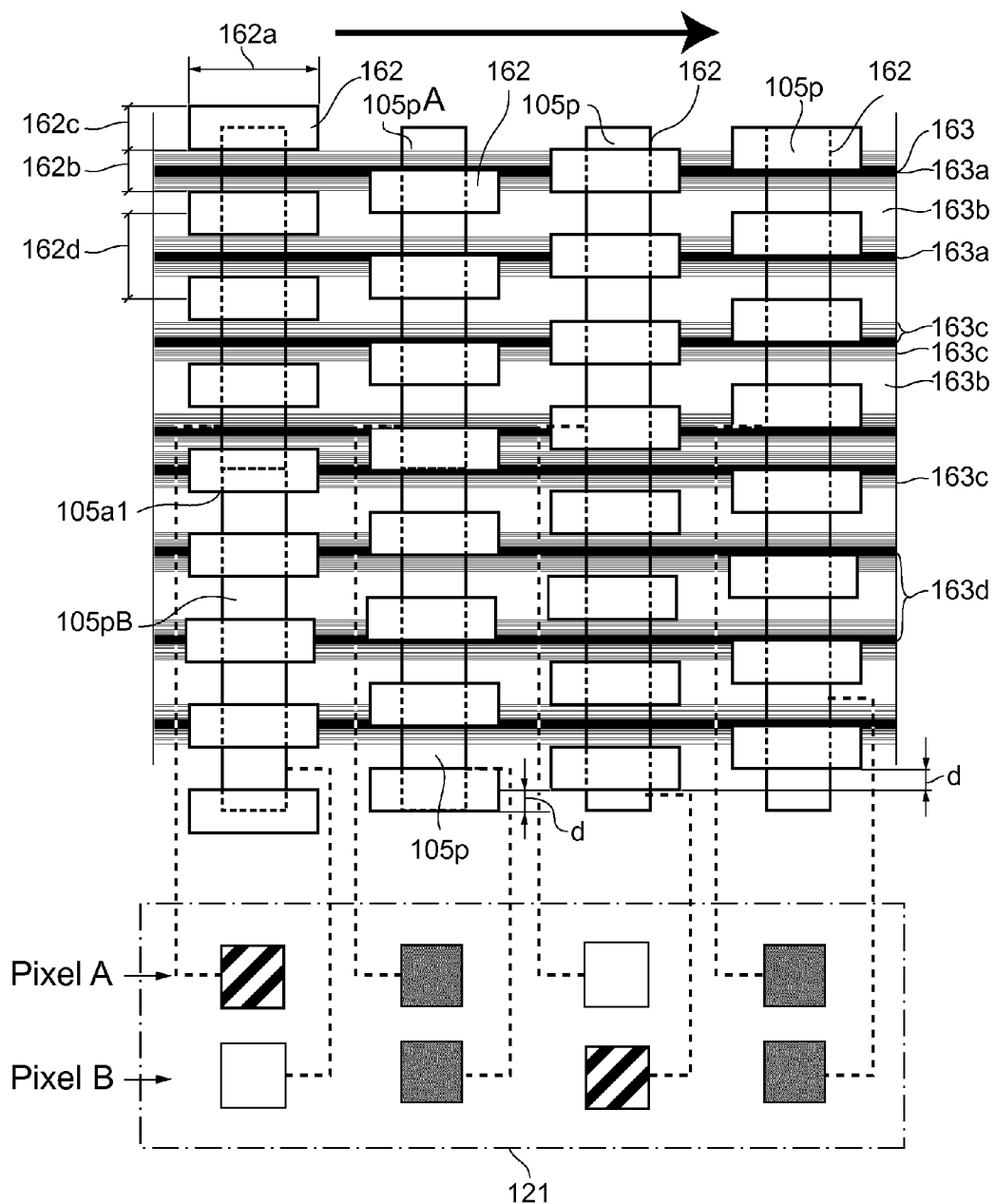
FIG. 3a shows a portion of the detector and a systematic displacement of the analyzer grating of adjacent detector strips

FIG. 3a shows a portion of the detector 105 comprising four detector strips 105a, the figure essentially viewed in a direction of incident x-ray beams 122 towards the detector 105, essentially in a negative z-direction according to the coordinate system of FIG. 2a and FIG. 2b. Four analyzer gratings 162 are arranged in association to these detector strips 105a, i.e. they are arranged in manner along the detector strips 105a in a second direction x to alternately cover and not cover the detector strips 105a with the openings 162b and closures 162c of the analyzer gratings 162. Further, each detector strips 105a are built up by a plurality of detector 105 pixels 105p arranged side-by-side in an x-direction as seen in the figure. To facilitate the illustration of the set up, the pixels have been made essentially rectangular. However, they may have any other type of shape. In one embodiment the analyzer gratings 162 are arranged directly on the detector strips 105a, for instance by a snap-fit connection between the analyzer gratings and the detector strips, but in another embodiment there is a slight distance between the detector strips 105a and the analyzer gratings 162. In yet another embodiment, the analyzer gratings 162 are arranged directly on the post-collimator 106b which in turn is arranged directly on the detector 105. According to the embodiment of FIG. 3a, the analyzer gratings 162 are arranged slightly displaced relative to each other in systematic manner in an x-direction, perpendicular to the scan direction, wherein the displacement is essentially equal for two consecutive detector strips 105a with analyzer gratings 162. The displacement distance d, i.e. the displacement of grating slits of the analyzer gratings 162 along a plurality of detector strips 105a is defined such that the plurality of detector strips 105a with analyzer gratings 162 samples an entire fringe period 163*d* of interference fringes 163 generated by a phase grating and displaced by a phase gradient in the object 108 when the object 108 is scanned during the scanning movement in the y-direction. In this manner, no additional scan is required in the x-direction according to e.g. a step-scan approach, since the fringe period 163*d* in the x-direction is scanned along with the scan movement in the y-z-plane.

The displacement d is a fraction of the fringe period 163*d* $p_f$, the fraction varying essentially between 1 and the number of detector strips 105*a* with analyzer gratings 162, i.e. such that $$\frac{p_f}{N} < d < p_f,$$

where N is the number of detector strips 105*a* with analyzer gratings 162. According to one preferred embodiment, the displacement d is between, $$\frac{p_f}{3} < d < p_f,$$

preferably $$\frac{p_f}{3}.$$

In FIG. 3*a* the fringes 163 are represented by the lines in the scan direction y. The darkest sections 163*a* of the lines represent the fringe maxima 163*a* of the fringe function and the middle of the white sections 163*b* represents the fringe minima 163*b* of the function. The sections surrounding the fringe maxima 163*a* thus represent an area of increasing/decreasing intensity 163*c* of the fringes 163. Hence, the fringe period 163*d* is thus defined as the distance between for instance two fringe maxima 163*a*. The fringes 163 of FIG. 3*a* are equal for each detector strip 105, which thus schematically shows each detector strip 105*a* scanning the same point in the object 108 at different points in time. In reality it is namely unlikely that the object 108 would be phase-homogenous over an area in an object 108 corresponding to four detector strips 105*a* during a scan. Rather, the fringe pattern will vary between each detector strip 105. According to one embodiment, the period of the analyzer grating 162 is the same as the period of the interference fringes 163 $P_f$, i.e. wherein the width of the grating openings 162*b* corresponds to the width of the fringes 163, i.e. half the fringe period 163*d*, comprising the fringe maxima 163*a* and the section surrounding the fringe maxima 163*a*. The pixels 105*p* of each detector strip 105*a* are adapted to sense the intensity of the fringe function and transmit a corresponding signal to a control unit 121. In the figure, such signal may correspond to a sensed fringe maxima 163*a* as in pixel 105*p* A in detector strip 105*a*1, a sensed intensity corresponding anywhere between an intensity maxima and minima as for instance in pixel 105*p* A and B in detector strip 105*a*2, or an intensity minima as in for instance in pixel 105*p* B of detector strip 105*a*, as shown in the squares corresponding to the sensed data by the control unit 121. The location of the interference fringes 163 in each pixel is deduced from the detected signals from a number of detector strips at the same point in the object. The displacement of the interference fringes 163 in each pixel can then be calculated by comparing to a reference scan. An example of wherein how this can be illustrated is seen in for instance detector strip 105*a* and detector strip 105*a*2, wherein both signals relating to intensity maxima and intensity minima are detected from pixels 105*p* in the same detector strips 105*a*. Given the constant fringe period 163*d* along each detector pixel 105*p*, the only explanation can be that there is a difference in phase shift between the two pixels. The differential phase shift Φ' in the object can be calculated according to $$\Delta p_f \approx \Lambda d_n \times \alpha = \Lambda d_n \frac{\lambda}{2\pi} \Phi',$$

with the fringe displacement $\Delta p_f$ deduced from the displacement of the fringe function over the entire fringe period for a function wherein an object has been scanned, i.e. placed in the x-ray beam, compared to a reference scan, wherein no object or a homogeneous object has been scanned. The actual phase shift in the object Φ may then obtained by integration of Φ', wherein a phase contrast signal may be calculated for each pixel 105*a*.

According to another embodiment, the intensity maxima and minima are simply arranged in an image corresponding to the object wherein phase shift occurs, for the operator of the imaging system to interpret and identify interesting areas by the aid of this information. The absorption contrast is detected in the scan direction, i.e. by averaging over the number of detector strips 105*a* required to cover an entire fringe period 163*d*, wherein the average value of the intensity over the pixels 105*p* of these detector strips 105*a* generate the absorption contrast one position of the image.

Figure 3B:
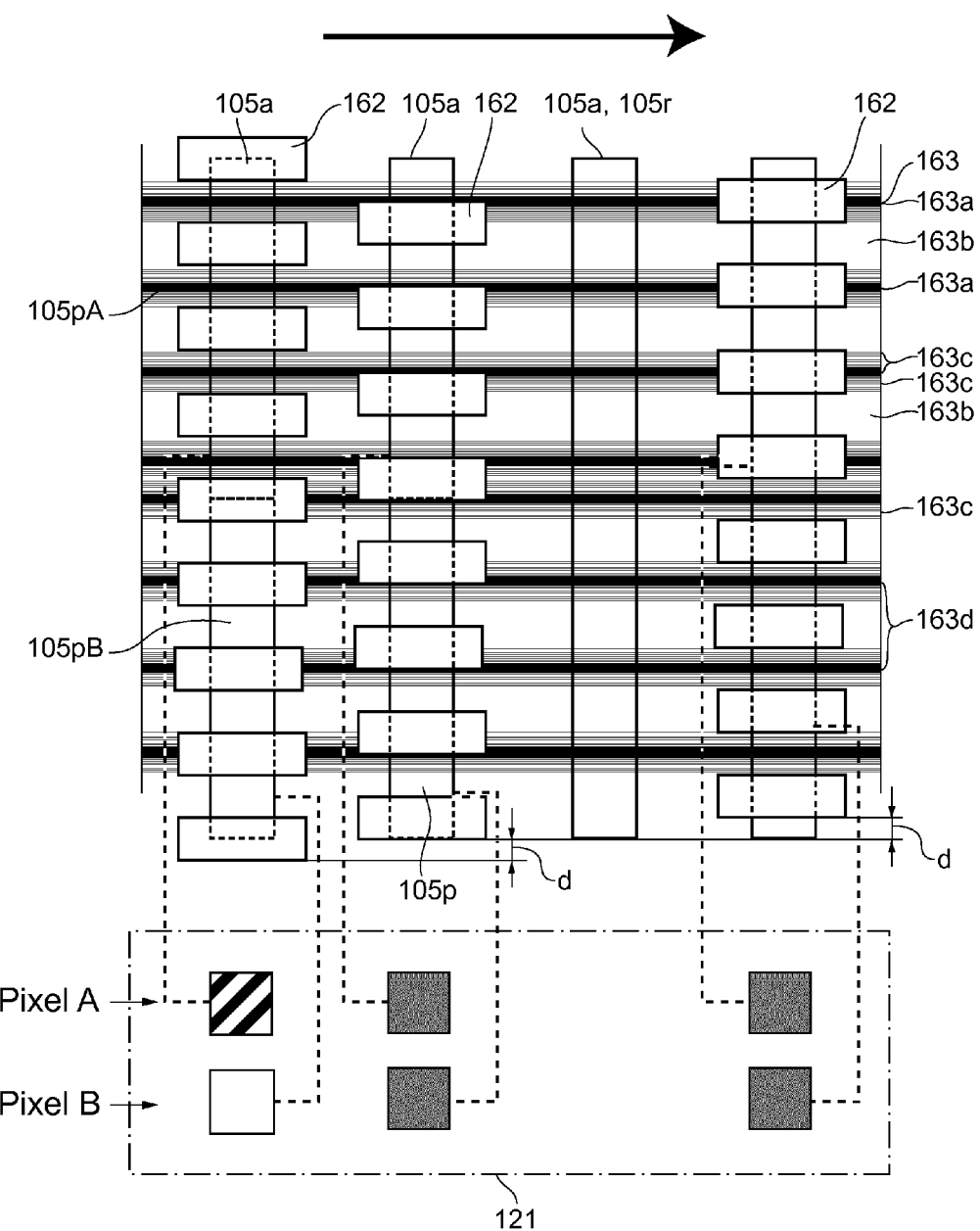
FIG. 3b shows portion of the detector and a systematic displacement of the analyzer grating of non adjacent detector strips

FIG. 3*b* shows a portion of the detector 105 similar to that of FIG. 3*a*, and a systematic displacement of the analyzer gratings 162 of two consecutive detector strips 105*a* with associated analyzer gratings 162, where at least one detector strip 105*a*, is arranged between two consecutive detector strips 105*a* upon which no analyzer grating 162 has been arranged. Hence, the analyzer gratings 162 does not have to be arranged on every detector strip 105*a* in the detector 105, i.e. on adjacent detector strips 105*a*, and the displacement d can thus be measured between two consecutive detector strips 105*a* upon which an analyzer grating 162 is arranged. Further, the order of consecutive detector strips 105*a* with analyzer gratings 162 may be random. However, the total number of detector strips 105*a* with analyzer grating 162 must be sufficient to cover an entire fringe period 163*d* of interference fringes 163. According to one embodiment, wherein the displacement is set to $$\frac{p_f}{3},$$

at least three detector strips 105*a* would be required.

Figure 3C:
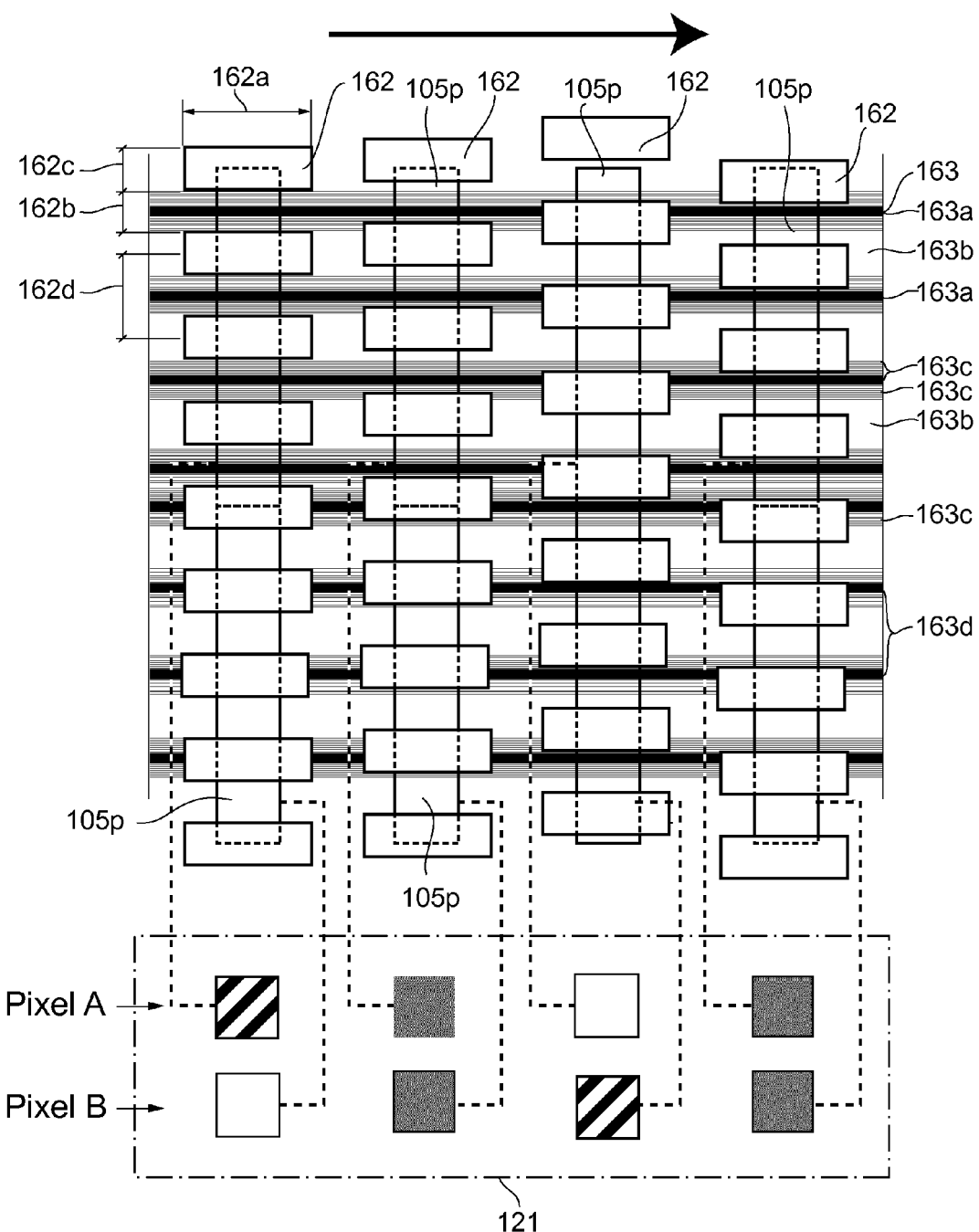
FIG. 3c shows a portion of the detector and a random displacement of the analyzer gratings 162 of adjacent detector strips

FIG. 3*c* shows a portion similar to that of FIG. 3*a* of the detector 105, but wherein the displacement d between two consecutive detector strips 105*a* with analyzer gratings 162*s*, in this case adjacent detector strips 105*a*, are displaced relative to each other in the second direction in an arbitrary manner, wherein the arbitrary manner comprises a random displacement. The only restriction on the randomness of the displacement is that when the summarizing all strips with analyzer gratings 162 they sample an entire fringe period 163*d* of interference fringes 163 generated by a phase grating and displaced by a phase gradient in the object 108 when the object 108 is scanned. That is, the random displacement needs to be uniformly distributed and range over the entire fringe period. In order for phase grating 161 imaging to function for a detector 105 with a random displacement of analyzer gratings 162, the system needs to be calibrated accordingly such that the exact positioning of the analyzer gratings is known by a processing device (not shown) which generates the data necessary for displaying an image. Such calibration may for instance be implemented by the placing of a test object with known phase shift in the x-ray beam. According to one embodiment, any type of placement of analyzer gratings, systematic or random, may preferably be calibrated according to this or other methods. In a similar manner to that of FIG. 3b, the random displacement of analyzer gratings 162 may occur on a random or arbitrary order of consecutive detector strips 105a with analyzer gratings 162 as well.

FIG. 3d shows a portion of the detector 105, wherein only two detector strips are shown. Analyzer gratings 162 have been arranged in a crosswise manner over the entire length of the detector strips 105a2 as seen in the figure, such as the grating lines are arranged in the x-direction to cover the entire image field in this direction. The grating lines between two detector strips 105a2 with crosswise arranged analyzer gratings 162 are displaced a distance $d_2$ (not shown) over a plurality of detector strips 105a in the scan direction, such that an entire fringe period 163d in the y-direction is covered by the openings 162b of the crosswise analyzer grating 162ds. Preferably, the displacement $d_2$ is a fraction of the fringe period 163d $P_{f2}$, in the y-direction similar to the displacement d previously described, wherein the fraction varies essentially between 1 and the number of detector strips 105a2 with crosswise analyzer gratings 162d, i.e. such that $$\frac{P_f}{N} < d < P_f$$

where N is the number of detector strips 105a with analyzer gratings 162. According to one preferred embodiment, the displacement d is in the range $$\frac{P_{f2}}{3} < d < P_{f2},$$

preferably $$\frac{P_{f2}}{3}.$$

In order to generate the interference fringes 163 in a y-direction for a detector strip with analyzer gratings in this direction, a corresponding second phase grating 161 needs to be arranged with grating lines in a y-direction. Hence, the direction of the phase grating(s) need to vary with respect to the direction of the analyzer gratings. According to one embodiment, such second phase grating 161 may be arranged in the proximity to the phase grating 161 as previously described, in a crosswise manner together with a first phase grating wherein a cross pattern of interference fringes are generated (not shown). Thus, by the aid of this set up, in one single scan, phase contrast detection is now possible in two dimensions along with the absorption contrast detection, to further enhance the ability to detect risk areas and abnormalities in a scanned object.

Figure 4A:
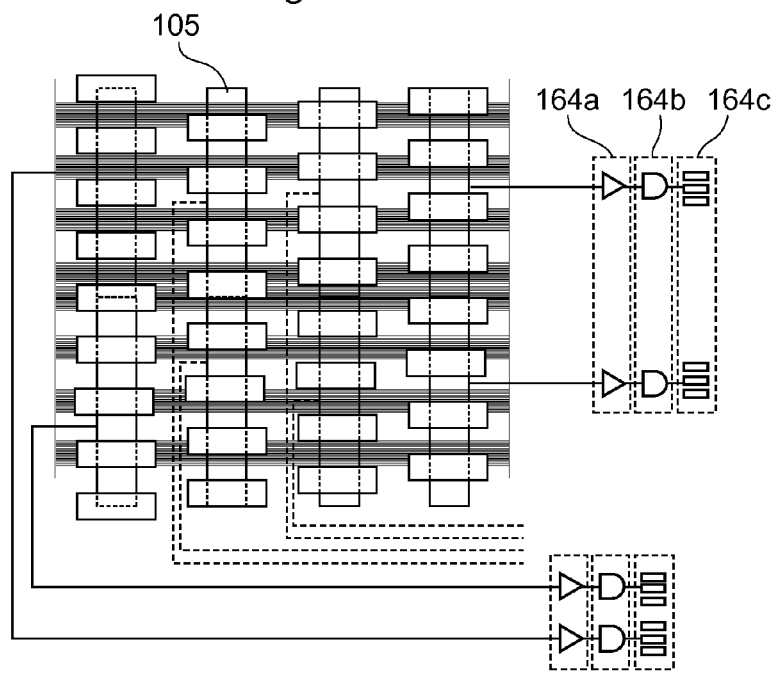
FIG. 4a shows the detector and a set up for energy weighting

In FIG. 4a a detector 105 arrangement according to one embodiment of the invention is illustrated for enhancing phase contrast information. As has previously been described, the so-called Talbot distances can be described as:

$$d_n = \frac{D_n L}{L - D_n}, \text{ where } D_n = \frac{np_1^2}{2\eta^2 \lambda}, n = 1, 3, 5,$$

The photon energy is inversely proportional to the x-ray wave length ($\lambda$). The relationship between $\lambda$ and $d_n$ thus implicates that there is an optimal energy $E_0$ for a given distance between a phase grating 161 and the analyzer grating 162. In a fix system according to one alternative embodiment of the invention, wherein the relative distance between the phase grating 161 and the analyzer gratings 162 is not adjustable, the efficiency of the phase contrast detection varies with the energy spectrum of the photons impinging on the detector 105 due to the varying visibility of the fringe function with the energy. The energy spectrum varies for instance with the setting of the acceleration voltage of the x-ray source 104 by an operator prior to a scan or gradients in breast thickness. Further, variations may also be caused by a so-called automatic exposure control (AEC) when implemented in the system, wherein the x-ray flux is optimized based on the breast thickness, sensed by the detector 105 during the beginning of scan by adaptively changing the x-ray source 104 acceleration voltage. An AEC is important when acquiring high quality absorption images and must therefore function parallel to a phase contrast detection functionality. The detector 105 assembly according to FIG. 4a proposes a detector 105 with energy weighting capabilities to overcome this limitation. According to a simplified arrangement, the pixels 105p of each detector strip 105a in the detector 105 is connected to an amplification block 164a, a comparator block 164b, and a counter block 164c. As an x-ray source 104 irradiates an object 108 and the detector 105 with an x-ray beam 122. The x-ray beam 122, containing photons with a certain energy spectrum is filtered by the object, and phase shifts of the photons may further occur. Thus, the photons carry relevant information when incident onto the detector 105. A signal is created based on the energy of the photon in the detector pixels. The pixel 105p signals are readout by first being amplified by an amplifier. After amplification the signal may be altered by a band pass filter or shaper, wherein signal to noise ratio is improved by suppressing high frequencies. After being amplified, the amplitude of the signal is compared to threshold levels in a comparator block, whereupon the comparator outputs 1 if the signal is above a threshold, and 0 if the signal is below the threshold. A photon pulse counter then increases its number every time the input changes from 0 to 1. With the aid of comparators, it is possible to count each photon having an energy within a certain energy interval.

Figure 4B:
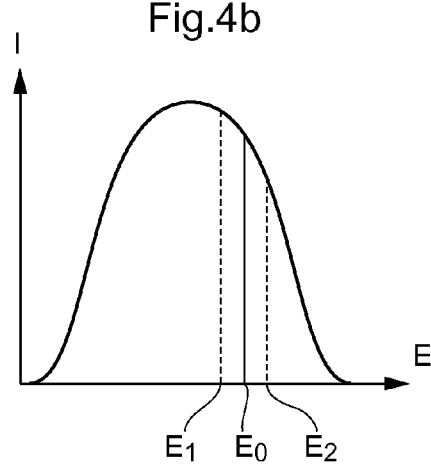
FIG. 4b shows energy distribution of photons of an x-ray source

In FIG. 4b a shows the energy spectrum of incident photons on a detector according to one embodiment of the x-ray imaging apparatus. The optimal energy is denoted $E_0$ a lower threshold is denoted $E_1$, a higher threshold is denoted $E_2$. Preferably, the photons having an energy within the energy interval $E_1$ to $E_2$ relevant for phase contrast is assigned a higher weight for the phase contrast image effect, by either reading out or by using only photons within this energy interval. The setting of the energy interval in the may be adjustable to comply with non-fix systems wherein the distance $d_n$ is adjustable. However, the width of the energy interval may also depend on the setting of the x-ray source, wherein a higher acceleration leading to a larger flux or intensity of photons, adjusts the energy interval to be more narrow and closer to the optimal energy $E_0$. Hence, as the flux increases, a higher amount of photons with energy close to $E_0$ will impinge the detector such that the quality of the image may increase. If the flux of photons is low, however, photons within a wider energy interval will have to be included to enhance the image quality.

According to another embodiment, the content of the photon pulse counters may be readout to a control unit 121 for optimally weighting the photons, for image processing and presentation. Preferably, the photons having an energy within the energy interval relevant for phase contrast is assigned a higher weight for the phase contrast image effect, wherein the photons having an energy within the energy interval extra relevant for absorption contrast is assigned a higher weight for the absorption contrast image effect. The weighting is based on pre set criteria in the control unit, for phase contrast photons may be assigned a 1 if inside the interval, and 0 if outside, and for absorption contrast, the photons having energies within the energy interval of extra importance to absorption contrast, are assigned a value higher than 0 according to one embodiment. The setting of the energy intervals may be adjustable to comply with non-fix systems wherein the distance $d_n$ is adjustable. This requires a set up of comparators and counters adapted to count photons within two energy intervals, a first energy interval defined by first lower threshold and a second higher threshold, and a second interval defined by a first lower threshold and a second, higher threshold. Assigning a higher weight, may, especially for the case of phase contrast photons comprise weighting by the factor 1.

According to another embodiment, three energy levels are used to count and weight photons according to increase phase contrast and absorption contrast effects, essentially dividing the energy spectra into three energy intervals, wherein the upper and lower limits are defined by infinitely high energies and 0 respectively. Preferably, photon with energies within the lower energy interval is filtered out and used for phase contrast. Photons with energies within the middle energy interval is counted and/or weighted positive, i.e. assigned a higher weight for absorption contrast and photons within the upper energy interval is counted and assigned a higher weight for phase contrast. The weighting of phase contrast photons may include weighting with a factor 1.

Figure 5:
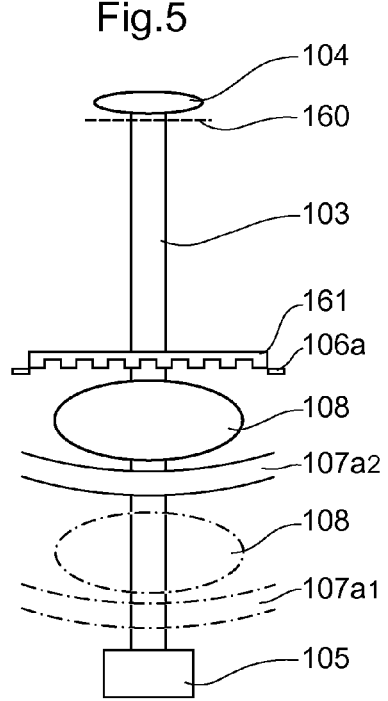
FIG. 5 shows a compression paddle in two alternative positions.

FIG. 5 shows a scan arm 103 with an x-ray source 104 and a detector 105 arranged at two positions, 107a and 107a2 respectively, essentially in each end of the scan arm 103. As known from previous figures, e.g. FIG. 2a, a phase grating 161 and pre-collimator 106a is arranged between the x-ray source 104 and the detector 105. Further, between the x-ray source 104 and the detector 105 a compression paddle 107a, 107b is arranged to move and/or compress the object 108 such as a breast in a vertical direction. In imaging arrangements to the present date, a compression paddle 107a, 107b is used for pressing the breast towards downwards towards a second compression paddle 107a, 107b, also known as the object 108 table. However, in order to increase the effect of the phase contrast in the x-ray image, the breast needs to be placed as far away from the detector 105. As described, For small α, the refraction causes a fringe displacement $$\Delta p_f \approx \Lambda d_n \times \alpha = \Lambda d_n \frac{\lambda}{2\pi} \Phi'$$

at a distance $\Lambda d_n$ from the object, where $\Lambda$ ranges from 0 for an object 108 placed in contact with the detector 105 to 1 for an object 108 at or upstream of the phase grating 161. Thus, the farther away from the detector 105, the larger the fringe displacement detectable by the detector 105. There is a trade-off between the absorption effect and the phase contrast effect depending on the vertical distance of the scanned object 108 from the analyzer grating 162. An increased distance from the detector 105 will diminish the absorption contrast effect due to scattering effects wherein valuable radiation that has passed the object 108 is lost. Therefore, the height of the compression paddles 107a, 107b should be adjusted based on and prior to the preferred type of scan to be performed. This could be implemented such that the height is automatically adjusted based on the setting by an operator of the x-ray imaging system 101.

In the field of mammography, there is an increasing demand for three-dimensional (3D) information which can reduce distraction by anatomical structures and provide 3D localization. The proposed embodiments disclosed in this application could readily be implemented in known tomosynthesis solutions, wherein projection angles are generated with the purpose to create projection images when the x-ray source 104 irradiates each point in an object 108 from various angles.

The present invention should not be limited to extracting phase-contrast information from the detected signals of the interference fringes. One example of other information that may be available is information about the object scattering ability, so-called dark-field imaging, such as in. In dark-field imaging, the visibility of the detected periodic function, defined as $$V = \frac{I_{max} - I_{min}}{I_{max} + I_{min}}$$

where $I_{max}$ and $I_{min}$ are the intensity maxima and minima respectively, may be compared to the visibility of a reference scan and used to obtain the dark-field image.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An x-ray phase contrast imaging system comprising:
   a scan arm configured to move with respect to an imaging region;
   an x-ray source mounted to the scan arm;
   an x-ray detector mounted to the scan arm opposite the imaging region from the x-ray source, the x-ray detector including a plurality of detector strips arranged in a first direction of the x-ray detector, each detector strip further comprising a plurality of detector pixels arranged in a second direction of the x-ray detector;
   a phase grating disposed between the x-ray source and the x-ray detector;
   a plurality of analyzer gratings comprising grating slits, the analyzer gratings being mounted between the imaging region and the x-ray detector and configured to move with the x-ray detector; and;

a controller configured to move the scan arm and the x-ray source and the x-ray detector in the first direction, in order to scan an object in the imaging region;

wherein each of the plurality of analyzer gratings is arranged in association with a respective one of the detector strips with the grating slits arranged in the second direction; and wherein the grating slits of each analyzer grating offset in the second direction relative to the grating slits of other analyzer gratings.

2. The x-ray imaging system according to claim 1, wherein the grating slits of the analyzer gratings are displaced such that the detector strips sample an entire fringe period of interference fringes generated by the phase grating and displaced by a phase gradient in the object when the object is scanned.

3. The x-ray imaging system according to claim 1, wherein the grating slits of contiguous analyzer gratings are offset in the second direction in a systematic manner by a defined displacement distance d.

4. The x-ray imaging system according to claim 3, wherein the displacement distance d is defined by $$\frac{p_f}{N} < d < p_f,$$

where $p_f$ is a fringe period, and N is the number of detector strips that cover the fringe period in its entirety.

5. The x-ray imaging system according to claim 3, wherein the displacement distance d is $$\frac{p_f}{3}.$$

6. The x-ray imaging system according to claim 1, wherein the grating slits of contiguous analyzer gratings offset relative to each other in the second direction in an arbitrary manner, wherein the arbitrary manner comprises a random displacement d.

7. The x-ray imaging system according to claim 1, wherein adjacent analyzer gratings arbitrarily displaced relative to the detector strips in a first direction.

8. The x-ray imaging system according to claim 1, further comprising:
a pre-collimator arranged between the analyzer grating and the phase grating and a post-collimator arranged between the analyzer grating and the x-ray detector.

9. The x-ray imaging system according to claim 8, further comprising:
a source grating arranged between the x-ray source and the phase grating.

10. The x-ray imaging system according to claim 1, wherein the detector is adapted to count photons impinging on the detector strips and generate a signal corresponding to energy of impinging photons, and further including: a control unit configured to receive said signals and assign a weight to the phase-contrast image effect based on an efficiency at each of a plurality of x-ray energies.

11. The x-ray imaging system according to claim 1, wherein the analyzer gratings are each connected to a corresponding one of the detector strips by a snap-fit connection.

12. The x-ray imaging system according to claim 1, wherein each analyzer grating comprises several smaller units, adapted to be connected to each other during the manufacturing of the analyzer gratings.

* * * * *